US00PP09128P

United States Patent [19]

Reimer

[11] Patent Number: Plant 9,128

[45] Date of Patent: May 9, 1995

[54] NECTARINE TREE, 'SURE FIRE'

[76] Inventor: Steven P. Reimer, 22506 Dinuba Ave., Dinuba, Calif. 93618

[21] Appl. No.: 165,986

[22] Filed: Dec. 13, 1993

[51] Int. Cl.[6] ..... A01H 5/00
[52] U.S. Cl. ..... Plt./41.1
[58] Field of Search ..... Plt. 41.1

*Primary Examiner*—James R. Feyrer
*Attorney, Agent, or Firm*—Godfrey & Kahn

[57] ABSTRACT

A new and distinct variety of nectarine tree denominated varietally as "Sure Fire" and which is somewhat similar to the Mayfire nectarine tree [unpatented] with which it is most closely related, but which is distinguished therefrom, and characterized as to novelty by producing fruit which are mature for harvesting and shipment approximately 10 days later than the Mayfire nectarine tree under the ecological conditions prevailing in San Joaquin Valley of central California.

1 Drawing Sheet

BACKGROUND OF THE NEW VARIETY

The present invention relates to a new and distinct variety of nectarine tree denominated varietally as "Sure Fire", and more particularly to such a nectarine tree which produces a clingstone fruit which has a firm yellow colored flesh at commercial maturity, and which is principally characterized as to novelty by a date of ripening of approximately May 12 through May 15 at Dinuba, Calif.

Fruit growers have long recognized that the relative dates that various varieties of nectarines become ripe for harvesting is of extreme importance. In particular, it has long been recognized as desirable to provide a nectarine tree that bears fruit during a portion of the season later than other varieties having similar characteristics such that the fruit can be sent to market at a time when completion is at a minimum, and the best price can be negotiated. Additionally, large scale agriculture has long understood that additional economic benefit can be attained if the harvesting periods of particular orchards are spread over longer periods of time inasmuch as the capital expenditures required to harvest and transport produce from the orchards can be spread over an extended period of time resulting in an overall lower cost for the final product by increasing the uniformity of production throughout the entire season.

The new and distinct variety of nectarine tree hereof is characterized as to novelty by producing fruit which are somewhat similar in their physical characteristics to the Mayfire nectarine tree[unpatented], but which is distinguished therefrom by producing fruit which are mature for harvesting and shipment approximately 10 days later than the Mayfire nectarine tree when grown under the ecological conditions prevailing in the San Joaquin Valley of central California.

ORIGIN AND ASEXUAL REPRODUCTION OF THE NEW VARIETY

The inventor has spent a substantial portion of his professional life engaged in farming operations. In this regard, the applicant, during routine orchard operations in 1991, discovered what appeared to be a full tree mutation of the Mayfire nectarine tree [unpatented] growing within the cultivated area of his commercial orchard which is located near 22506 Dinuba Avenue, Dinuba, Calif. The fruit produced by full tree mutation was noted at the time to have desirable characteristics.

More particularly, it was noted that the mutated tree produced fruit which were mature for harvesting and shipment approximately 10 days later than the remainder of the trees in the orchard. The inventor marked the mutated tree for subsequent observation. To determine whether the traits of the newly discovered variety were true, the inventor, in June of 1992, removed budwood from the mutated tree and grafted it into several test trees which consisted of four year old Nemaguard peach seedling root stock and which were then growing in the same orchard of origin. In view of the well established nature of the Nemaguard peach root stock, the buds produced a substantial amount of growth with resulting development of floral buds by the fall of 1992, and subsequent bloom and fruit set in 1993. The inventor has observed these test trees, and the original mutated tree, and has evaluated the fruit produced therefrom, and it has subsequently been determined that the fruit produced from these test trees have the same identical characteristic as that produced by the original mutated tree.

SUMMARY OF THE NEW VARIETY

The "Sure Fire" nectarine tree hereof is characterized principally as to novelty by bearing fruit which have an attractive skin color and which further are ripe for commercial harvesting and shipment from approximately May 12 through May 15 under the ecological conditions prevailing in Dinuba, Calif.; the new variety maturing approximately 10 days later than the Mayfire nectarine tree at this same geographical location.

BRIEF DESCRIPTION OF THE DRAWINGS

The accompanying drawing is a color photograph of a characteristic twig bearing typical leaves which displays both the top and bottom surface coloration thereof. Further, the photograph displays five mature fruit showing their external coloration sufficiently matured for harvesting and shipment, and one fruit divided in an axially oriented plane which shows the flesh characteristics, all of the subject variety.

DETAILED DESCRIPTION

Referring more specifically to the pomological details of this new and distinct variety of nectarine tree, the following has been observed under the ecological conditions prevailing in the orchard of the inventor which is located near Dinuba, Calif. All major color code designations are by reference to the dictionary of color by Maerz and Paul published in 1930, common color names are also employed occasionally.

TREE

Size:

*Generally.*—Average. The size and growth habit of the present variety appears to be substantially similar to the Mayfire nectarine tree.

Form: Upright to upright spreading. In this regard the originally mutated tree is trained into a standard vase-shaped form. The eventual form and density is determined by pruning practices. The present trees are planted in a high density orchard. Dormant pruning has been carried out so that the trees are held to a height of approximately 12 feet. Approximately 3.5 to 4 feet of new growth occurred in the 1993 season. There further appeared to be no observable differences in the new growth pattern as between the new variety and the Mayfire nectarine trees which are growing in the same orchard.

Productivity: Productive.

Vigor: Vigorous.

Regularity of Bearing: Regular, and hardy under typcial San Joaquin Valley climatic conditions.

New Growth: Generally as noted above, — The new variety is similar to the Mayfire nectarine tree in that both varieties experience 3–4.5 feet of new growth each year.

Trunk:

*Diameter.*—Average.

Surface texture of bark: Relatively coarse.

*Lenticels.*—Generally — Numerous. Shape — oval. Size — approximately 4 to 10 millimeters in width, and approximately 2 to 3 millimeters in height. Surface Texture — Most of the lenticels are heavily calloused.

*Bark color.*—Variable, grey-brown [7-A, Plate 10] and occasionally a darker brown-grey, [8-E, Plate 10].

Branches:

*Size.*—Average.

*Internode length.*—Generally — average, approximately 26 to 32 millimeters. Surface Texture — Relatively smooth.

*Color.*—Mature branches — Variable from a dark brown, [8-J, Plate 11], to a dark grey, [7-A, Plate 9]. Current season shoots — Pale green, [19-K, Plate 5]. Shoot tip — Bright green-yellow, [19-L, Plate 3].

LEAVES

Size:

*Generally.*—Large.

*Average length.*—Variable, from 16.2 to approximately 19.5 centimeters including the petiole.

*Leaf width.*—Generally — Variable, from approximately 3.8 to 4.6 centimeters.

Thickness:

*Generally.*—Average.

Leaf form: Lanceolate.

Leaf tip:

*Shape.*—Acuminate. At times the apex of the leaf appears twisted sideways.

Leaf color:

*Upper leaf surface.*—Dark green, [23-L, Plate 9].

*Lower leaf surface.*—A light, grey-green, [22-L, Plate 6].

Marginal Form: The leaf margins are crenate. The crenations are low and regular. Further, double crenations may appear near mid-margin. The leaf margins are moderately undulate.

Leaf petiole:

*Length.*—Long, approximately 9 to 13 millimeters.

*Thickness.*—approximately 1 to 2 millimeters.

*Color.*—Light green on the upper petiole surface and within the petiole groove, [21-L, Plate 7]. The lower petiole surface is a light green, [19-G, Plate 6].

Leaf glands:

*Form.*—Mixed. Both reniform or globose glands can be found.

*Numbers.*—From 1 to 4 stalked globose glands are usually present on the petiole and are positioned just below the base of the leaf blade. Further, an additional 1 to 3 glands can be located along the basal margin of the leaf blade.

Gland position: Variable, however, most frequently it is alternate.

*Color.*—Shiny and bright green when young, [19-L, Plate 2], however, this color becomes darker and deteriorates with senescence.

Leaf Stipules:

*Length.*—Variable, from 8 to 11 millimeters.

*Form.*—Linearly lanceolate.

*Marginal form.*—Serrate.

*Color.*—Light green when young, [19-L, Plate 4], however, with advancing senescence the color changes to a brown-orange, [12-E, Plate 11]. The stipules are considered early deciduous.

FLOWER

Generally:

*Date of full bloom.*—Approximately Mar. 3, in 1993. This date of full bloom is about the same as the Mayfire nectarine tree at this same geographic location. Further, the date of bloom is considered average and somewhat slightly early in relative relation to other commercial nectarine varieties which are commonly grown in this same region.

Flower buds:

*Generally.*—Large in size.

*Form.*—Conic, and free from the bearing stem. The flower buds are further considered hardy under normal San Joaquin Valley climatic conditions.

Bud scales:

*Color.*—Brownish-grey, [15-C, Plate 8].

*Surface texture.*—Very pubescent.

Flower size:

*Generally.*—Large.

Form: Showy type.

Diameter of flowers at full bloom: Variable, approximately 37 to 41 millimeters.

Bloom Quantity: Abundant.

Flowers per node: Variable, from 1 to 4 flowers may be found, although normally 2 flowers are present.

Petal size:

*Generally.*—Large.

*Length.*—Approximately 20 to 24 millimeters.

*Width.*—Approximately 17 to 19 millimeters.

*Form.*—Variable, although it frequently appears ovate.

*Petal number.*—Normally 5 petals are present, although in some instances semi-petals are present. The semi-petals are usually much narrower than the normal petals.

*Color.*—Generally — Light pink, [1-D, Plate 7]; however, a darker rose color may appear basally, [1-E, Plate 3]. The petals become darker with senescence especially basally.

*Petal margin.—Form.*—Generally undulate. This is especially noticeable apically.

*Petal.—Apex.*—Rounded, and somewhat domed.

Petal claw:

*Form.*—Short and truncate.

Pedicel:

*Length.*—Short; approximately 2.5 to 3.5 millimeters.

*Thickness.*—approximately 1 to 1.5 millimeters.

*Color.*—shiny green, [19-L, Plate 5].

*Surface texture.*—glabrous.

Nectaries:

*Color.*—Orange, [10-C, Plate 12]. The nectaries become darker with advancing senescence.

Calyx:

*Surface texture.*—Glabrous and rugose.

*Color.*—greenish basally, [19-L, Plate 3], and sometimes speckled with maroon spots on the upper portion of the calyx cup, [7-H, Plate 5]. Surface texture — Pubescent. The pubescence is long and grayish.

Sepals:

*Size.*—Large and ovate in shape.

*Color.*—Variable, occasionally greenish in color, [18-L, Plate 4], but maroon speckling may appear, [7-H, Plate 4], and grayish colored pubescence may be evident. Occasionally the sepals have full maroon appearance [7-H, Plate 4].

Anthers:

*Size.*—Average.

*Color.*—A red color appears dorsally, [5-K, Plate 11] and a tan color appears ventrally, [11-H, Plate 5].

*Pollen color.*—Golden-yellow, [10-L, Plate 4]. The pollen is considered abundant.

Stamen length: Variable, approximately 15 to 18 millimeters. The stamens are generally slightly longer than the pistil.

Filaments:

*Color.*—Light pink, [1-B, Plate 7] when young, and becomding darker with advancing senescence, [2-H, Plate 4].

Pistil length: Variable, from 16 to 18 millimeters including the ovary.

*Color.*—Pale, yellow-green, [17-G, Plate 2].

*Surface texture.*—Glabrous.

Pollen production:

*Generally.*—Abundant. The new variety appears from all indications to be self-pollinating.

FRUIT

Maturity when described: Ripe for harvesting and shipment May 12 through May 15 in 1993.

Size:

*Generally.*—Large, and somewhat asymmetrical with one side usually appearing slightly larger than the other. In relative comparison to the fruit produced by the Mayfire nectarine tree, the present variety is noticeably larger. Further, the present variety produces fruit which are larger than the fruit produced by the Mayfire nectarine tree even when the same tree is girdled. Presently the new variety, and the Mayfire nectarine tree grows side-by-side in the same orchard. Both varieties are girdled.

*Average cheek diameter.*—Approximately 58 to 66 millimeters.

*Average diameter in the suture plane.*—Approximately 61 to 65 millimeters.

*Average diameter in the axial plane.*—Approximately 59 to 63 millimeters.

Form: Asymmetrical with one side usually appearing larger than the other. The fruit is considered ovate in its lateral aspect and oval to nearly globose in its apical aspect.

Suture:

*Generally.*—The suture appears as a continuous line which extends from the base to the apex. The fruit suture is substantially deeper and at times clefted over the basal shoulder and within the stem cavity basin.

*Color.*—Generally — Dark red, [7-L, Plate 4]. This color is uniform throughout its entire length.

Ventral surface:

*Surface texture.*—Relatively smooth in the area from the apex to the basal shoulder. However, the ventral surface may be creased over the shoulder area. Generally no lipping is evident.

Stem cavity:

*Size.*—Small.

*Width.*—Approximately 23 to 27 millimeters.

*Length.*—Approximately 25 to 28 millimeters.

*Depth.*—Shallow, approximately 8 to 10 millimeters.

*Form.*—Variable from oval, to nearly globose.

Fruit base:

*Form.*—Slightly truncate.

*Base angle.*—Variable, the base angle usually appears at a right angle, although occasionally the base angle may be slightly oblique relative to the fruit axis.

Fruit apex:

*Generally.*—Rounded with the pistil point located apically.

*Shape.*—Slight depressions are present on both sides of the apex. Further, the apex is slightly depressed and usually appears just below the level of the apical shoulders.

Fruit stem:

*Size.*—Average.

*Stem length.*—Approximately 9 to 11 millimeters.

*Thickness.*—Approximately 2.5 to 3 millimeters.

*Color.*—Variable, from a light green, [21-L, Plate 3] to a brownish green, [15-L, Plate 7].

Fruit skin:

*Thickness.*—Average.

*Texture.*—Glabrous.

*Flavor.*—Neutral, although it may occasionally taste slightly acidic.

Tenacious to flesh: Yes, at commercial maturity.

Tendency to crack: Not observed.

Skin color:

*Generally.*—The skin color is moderately uniform. Approximately 75% to 95% is blush colored. The blush colored pattern varies, from a solid washed pattern to variable dappling and striping. The darkest color is a deep burgundy red, [6-L, Plate 10] which lightens to a bright red, [4-L, Plate 10]. Numerous light colored dots and speckles are present over the fruit surface and are concentrated normally over the apical end of the fruit. The speckling, which can be characterized as russetting is essentially identical in amount to that found on the fruit which is produced by the Mayfire nectarine tree. Although russetting varies widely from year to year depending upon climatic conditions, the russetting observed in the fruit of the new variety and the fruit produced by the Mayfire nectarine tree was considered moderate in 1994. A light yellow ground color may be present over 5% to 25% of the fruit surface, [10-K, Plate 2]. Occasionally, a pale green color is sometimes present although this color is not particularly distinctive. The new variety is more highly colored than that of the variety Mayfire. Further, the blush pattern observed on the fruit produced by the two trees, when compared during the 1994 season, revealed that the blush of the Mayfire covered approximately 85% to 90% of the fruit surface. In relative comparison, the blush of the new variety covered approximately 95% to 100% of the fruit surface.

Flesh color: Generally — Uniform and yellow, [10-J, Plate 3], although a slightly darker yellow color is present within the stone cavity. Numerous light colored tender fibers can be detected throughout the flesh. The flesh color of the new variety of nectarine tree, in the vicinity of the stone cavity, was substantially identical to the remainder of the flesh color.

Flesh texture: Medium. The flesh is firm and crisp at commercial maturity and becomes increasingly softer and juicy with advancing age.

Ripening:

*Generally.*—Even.

Flavor:

*Generally.*—Sweet and having moderate acidity.

Aroma:

*Generally.*—Moderate and pleasant.

Eating quality: Considered good, as compared with other nectarine tree varieties which ripen at approximately the same time of the season.

STONE

Attachment: The subject variety is considered to be a cling stone at commercial maturity and becomes semi-freestone with advancing age.

Stone size:

*Generally.*—Average.

*Length.*—Approximately 33 to 37 millimeters.

*Width.*—Approximately 25 to 28 millimeters.

*Thickness.*—Approximately 17 to 19 millimeters.

Fibers:

*Generally.*—Numerous fibers are attached to the stone over the entire surface. The fibers are especially numerous on both the dorsal and ventral sutures and over the basal and apical areas of the stone.

Form:

*Generally.*—Ovate.

Stone base:

*Shape.*—Truncate. The base angle is slightly oblique to the stone axis.

Hilum:

*Size.*—Large and appearing oval in form.

*Surface texture.*—The entire hilum is heavily eroded.

Apex:

*Generally.*—The form and tip of the apex is acute.

Stone sides:

*Generally.*—Variable and often considered slightly unequal.

Stone surface:

*Surface texture.*—Moderately rough with numerous oval shaped pits appearing laterally. As a general matter, a very deep wide groove appears laterally and is approximately 2.5 to 3.0 millimeters in width. This groove extends substantially parallel to and approximately 4 to 5 millimeters, below the ventral edge.

Ventral edge:

*Generally.*—The ventral edge is relatively wide and is approximately 6 to 8 millimeters in width at mid-suture. Several coalesced wings are present along the ventral edge and are normally more evident basally. These wings extend approximately 4 to 6 millimeters from the body of the stone.

Dorsal edge:

*Generally.*—A relatively wide and deep groove is present along the dorsal edge. The dorsal edge is approximately 2.5 to 3.5 millimeters in width at mid-stone but appears much more narrow over the apical shoulder. The aforementioned dorsal groove is subtended by two moderately rough ridges which are notched in several places along their length. The apical shoulders of the dorsal ridges are moderately eroded.

Stone color: Dry — Buff, [10-G, Plate 4].

Tendency to split: External split of the pits may appear occasionally but internal splits are common.

Fruit use: A fresh market nectarine for use in local and long distance shipping.

Keeping quality: Good.

Resistant to disease: No particular susceptibilities were noted.

Although the new variety of nectarine tree possesses the described characteristics as a result of the growing conditions prevailing in Dinuba, Calif., in the central portion of San Joaquin Valley of California, it is to be understood that variations of the usual magnitude and characteristics incident to growing conditions, fertilization, pruning and pest control are to be expected.

Have thus described and illustrated my new variety of nectarine tree, what I claim is:

1. A new and distinct variety of nectarine tree to be denominated varietally as "Sure Fire", substantially as illustrated and described, and which is characterized principally as to novelty by its production of fruit which are somewhat similar in their overall appearance to the fruit produced by the Mayfire nectarine tree [unpatented] from which it was derived as a chance mutation, but which is distinguished therefrom, and characterized principally as to novelty by producing fruit which are ripe for commercial harvesting and shipment approximately 10 days later than the fruit produced by the Mayfire nectarine tree at the same geographical location.

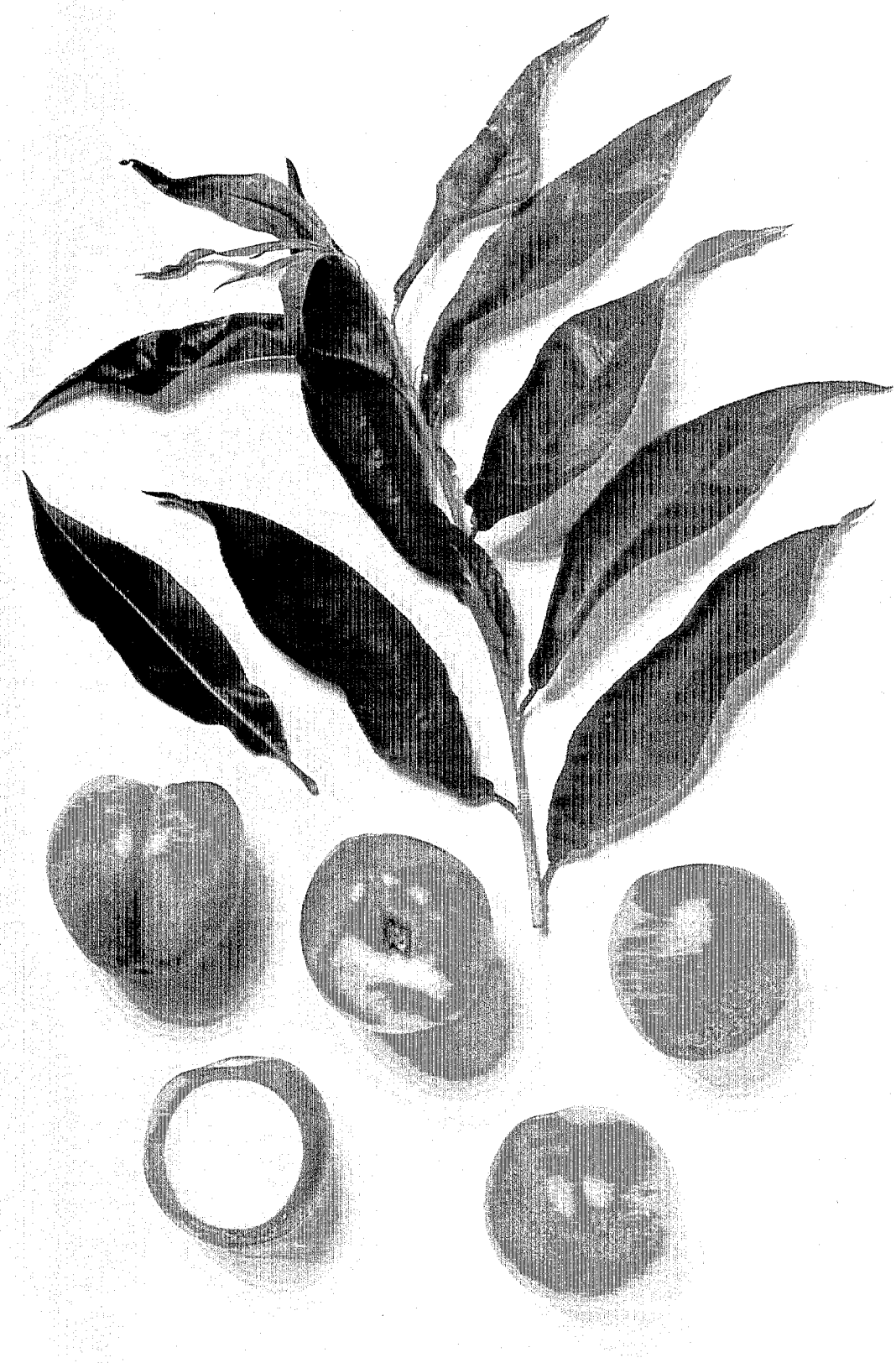

* * * * *